(12) United States Patent
Lin

(10) Patent No.: US 7,637,890 B2
(45) Date of Patent: Dec. 29, 2009

(54) SAFETY SELF-DESTROYING DISPOSABLE SYRINGE

(76) Inventor: Zuoqian Lin, Shangma Plastic Moulding Factory, Shangma Industrial Zone, Shikuang, Wenling, Zhejiang (CN)

( * ) Notice: Subject to any disclaimer, the term of this patent is extended or adjusted under 35 U.S.C. 154(b) by 0 days.

(21) Appl. No.: 11/720,327

(22) PCT Filed: Jan. 25, 2005

(86) PCT No.: PCT/CN2005/000392

§ 371 (c)(1),
(2), (4) Date: May 26, 2007

(87) PCT Pub. No.: WO2006/079257

PCT Pub. Date: Aug. 3, 2006

(65) Prior Publication Data

US 2008/0132837 A1      Jun. 5, 2008

(30) Foreign Application Priority Data

Jan. 25, 2005   (CN) .................... 2005 2 0068571 U
Jan. 25, 2005   (CN) .................... 2005 2 0068572 U
Jan. 25, 2005   (CN) .................... 2005 2 0068573 U

(51) Int. Cl.
*A61M 5/00* (2006.01)
(52) U.S. Cl. ..................................... 604/110
(58) Field of Classification Search .................. 604/110, 604/192–198, 240–243
See application file for complete search history.

(56) References Cited

U.S. PATENT DOCUMENTS 5,401,246 A * 3/1995 Mazur et al. ................. 604/110
6,752,784 B2 * 6/2004 Tsai ............................ 604/110

* cited by examiner

*Primary Examiner*—Matthew F Desanto
(74) *Attorney, Agent, or Firm*—Banger Shia

(57) ABSTRACT

The present invention provides a safety self-destroying disposable syringe, which consists of a hollow tube, a plunger fitting into the inside of the hollow tube and a rubber piston attached on the tip end of the plunger, and a needle holder attached on the front end of the hollow tube, wherein said needle holder is comprised of a cone base and a seat; said cone base has a Roll cone for fitting into the needle, and a circular base for fitting into the inside of the hollow tube, there are several O-rings attached on the contacting surface between them; there is a locating ring-groove built on the inside wall of the hollow tube approaching the front end for catching up the needle holder; said plunger has a conical head built on the front end, and said conical head has a circular barb built on the middle portion. The safety syringe provided by the present invention can be withdrew into the inside of the tube, and also suit to match to diversity of standard needles for replacing, it also has simple structure, easy manufacturing and convenient use with high safeness features.

14 Claims, 9 Drawing Sheets

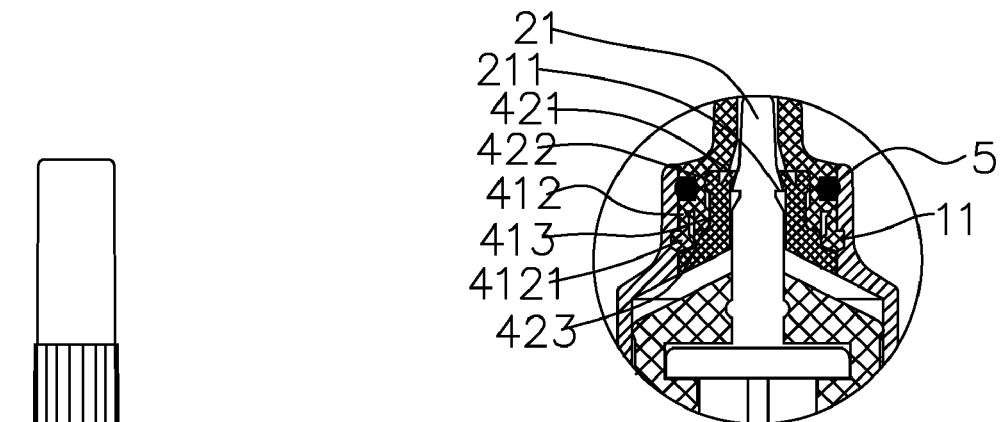
FIG. 2
FIG. 3
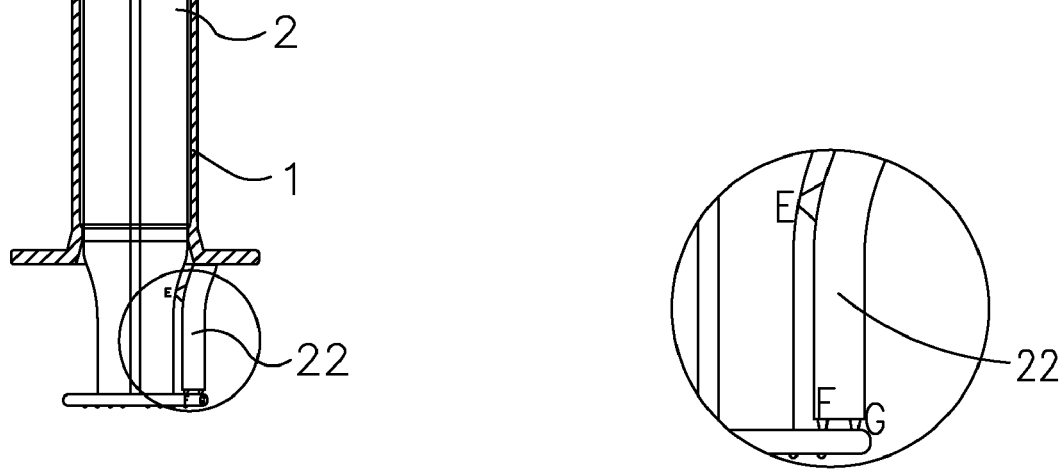
FIG. 1
FIG. 4

SAFETY SELF-DESTROYING DISPOSABLE SYRINGE

BACKGROUND OF THE INVENTION

1. Field of the Invention

The present invention relates to a hypodermic syringe, and more particularly to a safety self-destroying disposable syringe (called 'safety syringe' for short in following).

2. Description of Prior Art

It has been proofed by the practice of medicine that for avoiding human or animal crossly infecting in injection or withdrawing process, the hypodermic must use disposable injector facilitating to be disposed as garbage after using. In accordance with the conventional disposable syringes commonly used in the market so far, it is typically comprised of a hollow tube, a needle and a piston fitting into the inside of the hollow tube, but the vital problem of this kind of syringe is that the needle is kept into the outside after injection, relating to the sharpness of the needle, the air-opening needle attached on the syringe not only brings up some troubles in transporting and disposing these medical garbage, but also cause the medical workers to be stung unexpectedly and frequently, so that the second cross infection will become to be inevitable, especially to syringes used to those patients with heavy infection diseases (like aids, hepatitis, SARS and so on), it is a big hidden trouble in medicine to be regarded. It is proofed in practice that the unexpected harms occurred by the risky syringes is more than others.

Recent years, according to the discovery of repeat-using the disposable syringes by some evil persons, a safety self-destroying syringe was proposed in last century, in which the used self-destroying syringe is automatically destroyed or locked up without any possible to be used repeatedly. But there is a big shortcoming existing in these conventional self-destroying syringes that the needle holder has to correspond to the hollow tube one to one, it is impossible of replacing the needle holder for meeting the necessary of different patients, so that the injection operation becomes so complex to bring some troubles to the medical workers.

OBJECTS AND SUMMARY OF THE INVENTION

It is therefore a main object of the present invention to provide a safety self-destroying syringe, in which the hypodermic needle can be replaced with diversity of standard needles, and structure of the syringe is simple facilitating to manufacturing and use with high safeness.

For archiving the goal, the present invention provides a safety self-destroying disposable syringe consisting of a hollow tube, a plunger fitting into the inside of the hollow tube and a rubber piston attached on the tip end of the plunger, and a needle holder attached on the front end of the hollow tube, wherein said needle holder is comprised of a cone base and a seat; said cone base has a Roll cone for fitting into the needle, and a circular base for fitting into the inside of the hollow tube, there are several O-rings attached on the contacting surface between them; there is a locating ring-groove built on the inside wall of the hollow tube approaching the front end for catching up the needle holder; said plunger has a conical head built on the front end, and said conical head has a circular barb built on the middle portion.

Said cone base has several elastic catching lugs built on the bottom outside wall coordinating to the locating ring-groove of said hollow tube for engaging in, and an internal convex edge formed on the bottom rim of the inside wall; said seat is fit into the hollow inside of said cone base, and has an elastic clamper built on the internal front end, and a flange built on the external front end for fitting into the internal hole of said cone base, and a middle flange built on the middle portion for supporting outward the elastic catching lugs of said cone base.

Said cone base has several elastic catching lugs built on the bottom outside wall coordinating to the locating ring-groove of said hollow tube for engaging in, and a ring-groove built on the inside approaching the bottom with the width bigger than the sum of the fitting segment of the top portion of the seat and the distance of push-up; said cone base also has several elastic clampers built on the inside wall on the bottom; said seat is fit into the hollow side at the bottom side of said cone base with an external circular surface mating to the diameter of the ring-groove of the cone base, and has an internal convex edge formed on the bottom end for catching up the raised cone head of said plunger, within its length is bigger than the elastic catching lug such as the seat depart-off distance; said seat also has a column head built on the external wall of the top end for matching with the elastic catching lugs of the cone base, and a circumferential notch built on the bottom, within the size of the circumferential notch is in excess of the returning course of the elastic catching lugs of the cone base.

Said cone base has an upper flange built on the outside wall for matching to the front internal flange of the hollow tube, and a middle flange mating to the hollow cavity of the hollow tube, so between said upper and middle flanges a flat mesa is formed, and an internal convex edge formed on the bottom portion of the inside wall; said seat is fit into the hollow inside of said cone base, and has an elastic clamper built on the internal front end, and several elastic catching lugs built on the external low wall coordinating to the locating ring-groove of said hollow tube for engaging in; said seat also has a front flange built on the front rim outward for matching with the internal diameter of said cone base, and a low flange built on the bottom portion.

The taper of said Roll cone is 6:1000.

Said elastic catching lugs can spread out and withdraw in; as spreading out they engage into the inside of the ring-groove of the hollow tube for locating the cone base on said hollow tube tightly; as withdrawing in, they slide out from the ring-groove of the hollow tube so as to release the cone base from the hollow tube.

The engaging portions of said elastic catching lug and the ring-groove of the hollow tube can be in rectangle, ladder, circle, ellipse or polygon in sectional view.

Said internal convex edge built on the inside wall of said cone base is matched between the front and middle flanges of the seat and freely moves in there, and also mates with the front flange of the seat.

Said seat fitting into the inside of said cone base just can move in the gap between said elastic catching lugs and the ring-groove, as getting to lowest point, the inside beveled surface of the bottom end of the seat exactly backs up the back of the elastic clamper of said cone base up tightly.

The flange of said hollow needle is a right step engaging on the front flange of said cone base to overlap the middle flange, within the shape of the engaging portion in sectional view can be in rectangle, ladder, circle, ellipse or polygon.

Said plunger has tree knock-off notches built on different surfaces alternatively at the middle portion.

Said plunger has a safety baffle built on the back end axially with several knock-off notches on the connection portion for contacting with the back end of the hollow tube.

According to applying above-mentioned structure, comparing with the conventional safety syringe in the market so far, the present invention has following advantages: first, the elastic catching lugs distributed on said cone base (or said seat) symmetrically engage into the ring-groove of the hollow tube tightly to keep the cone base from drawing out or in, or rotating right-left, meanwhile the Roll cone head can match to diversity of standard hollow needles. O-ring located between the cone base and the hollow tube prevents the liquid from leaking. As drawing out the syringe after finishing the injection operation, said cone base is easy to be pulled into the inside of the hollow tube without any possible to be reused, so the self-destroying function is carried out. Second, just need to exert a bit pushing force on the plunger so that the cone head of the plunger enters the inside of the elastic clamper of the cone base to reduce the pain of the patient; next, the safety baffle attached on the rear end of the plunger can prevent the syringe from self-destroying unexpectedly before use or in a mistake operation. In one word, the safety syringe offered by the present invention can withdraw the needle into the inside of the hollow tube after using, and it can match to diversity of standard hollow needles in replacing, meanwhile the safety syringe has simple structure, easy manufacture and convenient use, and high safety features.

BRIEF DESCRIPTION OF THE DRAWINGS

FIG. 1 is a sectional view showing the sectional structure of the present invention.

FIG. 2 is an enlarged sectional view showing the structure of the engaging portion of the present invention.

FIG. 3 is an enlarged sectional view showing the knock-off portion of the plunger of the present invention.

FIG. 4 is an enlarged sectional view showing the safety baffle of the present invention.

DETAILED DESCRIPTION OF PREFERRED EMBODIMENTS

Referring to FIG. 1, a safety syringe provided of the present invention is consisted of a tube 1, a piston 3 fitting into the inside of the tube 1, a plunger 2 driving the piston 3 moving axially, and a needle holder 4.

Figure 5:
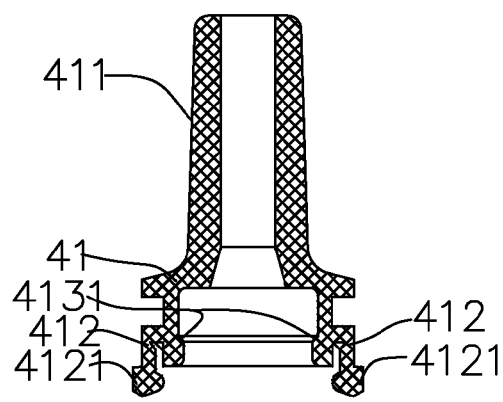
FIG. 5 is a sectional view showing the cone base of the present invention.

Referring to FIG. 2 to FIG. 5, said needle holder 4 is typically comprised of a cone base 41 and a seat 42. Wherein, said cone base 41 has a Roll cone head with 6:100 taper for matching to diversity of standard needles. Said cone base 41 also has two elastic catching lugs 412 built on the external bottom side, coordinating to said elastic catching lugs 412, said tube 1 has a ring-groove 11 built on the corresponding position; said elastic catching lug 412 has a right upper-edge engaging portion 4121 at the top side and a low beveled surface for matching to the responding surfaces of the ring-groove 11 of the tube 1. Said cone base 41 also has an internal convex edge 413 built on along the inside bottom rim; there is an O-ring 5 attached on the contacting surface between said cone base 41 and the tube 1.

Said seat 42 located at hollow inside of said cone base 41 is made of elastic material, in which an elastic clamper 421 is built on the internal front edge, and a front flange 422 is built on the external front edge outward for fitting into the internal hole of said cone base 41, within the external diameter of said front flange 422 is bigger than the inner diameter of the internal convex edge 413 of said cone base 41. In combination, said seat 42 is pushed upward axially from the bottom of said cone base 41 to extrude the front flange 422 under an extra force coming from the internal convex edge 413 of said cone base 41 to distort until the whole front flange 422 passes through the internal convex edge 413 to restore the original state. Meanwhile in the term of pushing up the seat 42, the middle flange 423 pushes the elastic catching lugs 412 outward to support the elastic catching lugs 412 engaging into the inside of the ring-groove 11 of the tube 1 so that the seat 41 is located on the inside of the tube 1 tightly without any possible to move and turn in any direction.

Said plunger 2 has a conical head 21 built on the front end, and said conical head 21 has a circular barb 211 built on the middle portion, as finishing the injection operation, said circular barb 211 exactly gets the topside of the elastic clamper 421 of said seat 42 so that they are interlocked together. Said plunger 2, as shown in FIG. 3, has three knock-off notches A B C built on different surfaces alternatively at the front portion for keeping the trunk rigidity and facilitating to molding and breaking up as drawing with a bit force. Said plunger 2, as shown in FIG. 4, also has a safety baffle 22 built on the rear end for preventing the syringe from self-destroying unexpectedly before use in a mistake operation in the packing or transportation, it works as a protection device. On the other hand, said safety baffle 22 has three knock-off points E F G for facilitating to breaking off after use.

Figure 6:
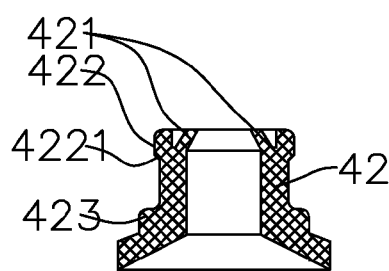
FIG. 6 is a sectional view showing the seat of the present invention.
Figure 7:
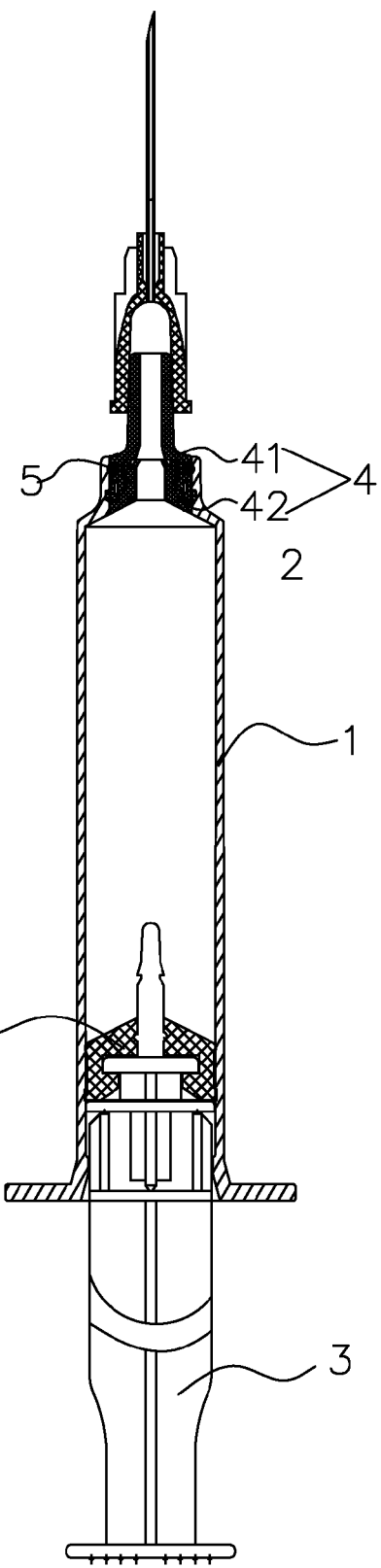
FIG. 7 is a sectional view showing the state after exhausting operation of the present invention.
Figure 8:
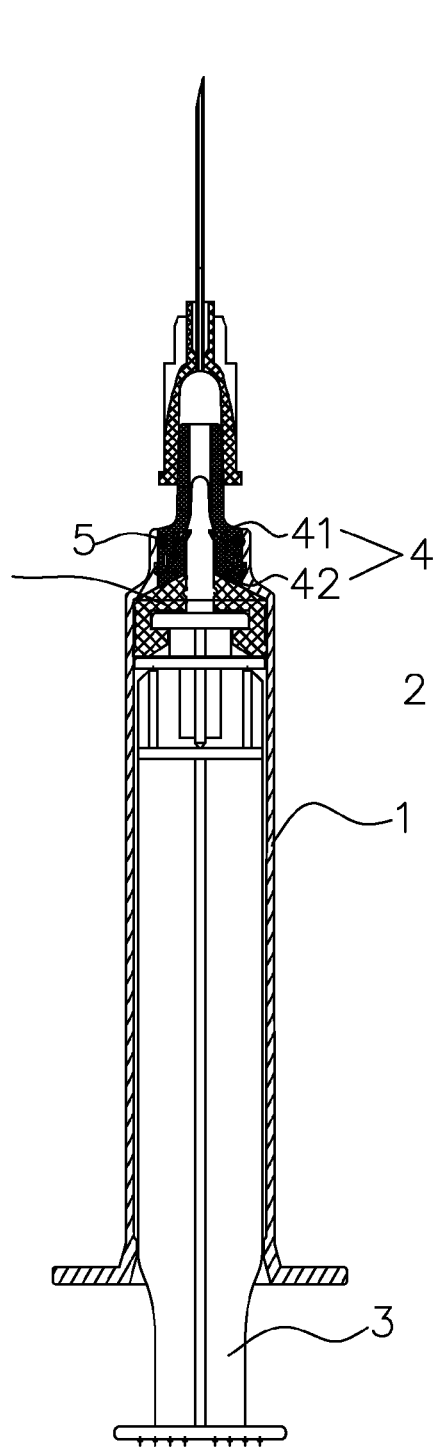
FIG. 8 is a sectional view showing the state after injecting operation of the present invention.
Figure 9:
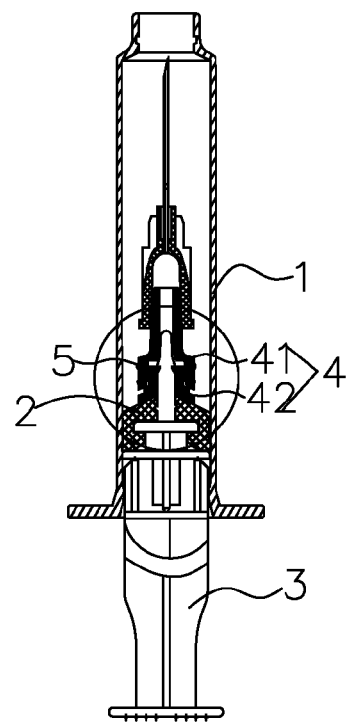
FIG. 9 is a sectional view showing the state of drawing the needle into the inside of hollow tube of the present invention.
Figure 10:
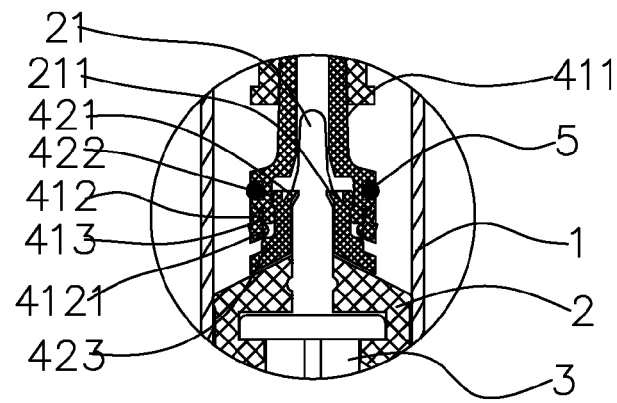
FIG. 10 is an enlarged sectional view of FIG. 9.
Figure 11:
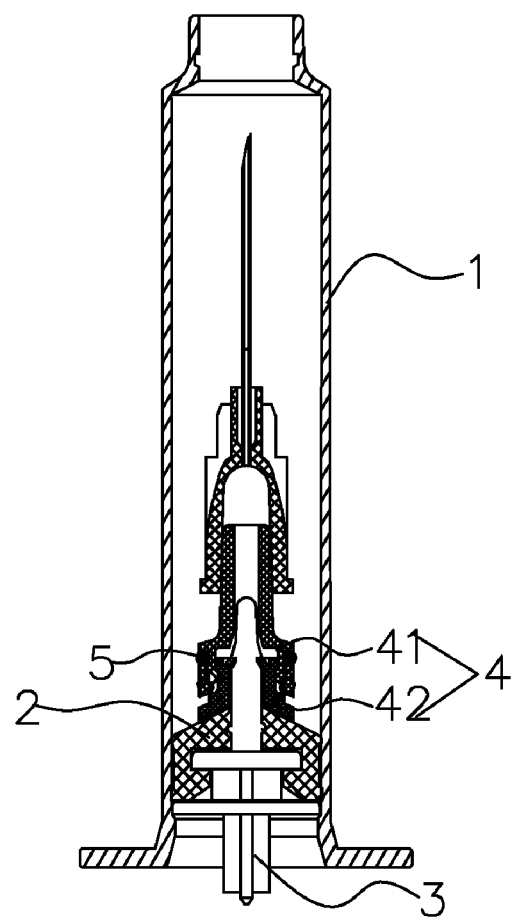
FIG. 11 is a sectional view showing the state of the safety syringe after breaking out the plunger of the present invention.

Referring to FIG. 5 to FIG. 11, as finishing sucking operation, break off the safety baffle 22. but in injection operation, after the plunger 2 pushed moves a certain distance, the crowned conical head 21 crowds out said elastic clamper 421 of the seat 42, and stretches into the hollow inner cavity of the seat 42 until the injection operation is finished, in this time, the circular barb 211 exactly gets the inside of the elastic clamper 421 of said seat 42 so that they are interlocked together. Next, pull backward the plunger 2, by means of the interlocking of the circular barb 211 and the elastic clamper 421, the seat 42 is drew to move downward, when the upper stopping point 4221 of the front flange 422 of the seat 42 is drew to touch with the low stopping point 4132 of the internal convex edge 413 of the seat 42, the middle flange 423 is departed from the elastic catching lugs 412 so that the elastic catching lugs 412 are withdrew back inward to slide out from the ring-groove 11 of the tube 1, at this time, just need to overcome the friction of the O-ring 5 and the inside wall of the tube 1, the seat 42 can be continued to move down until the whole needle is drew into the inside of the tube 1 to carry out self-destroying function.

Figure 12:
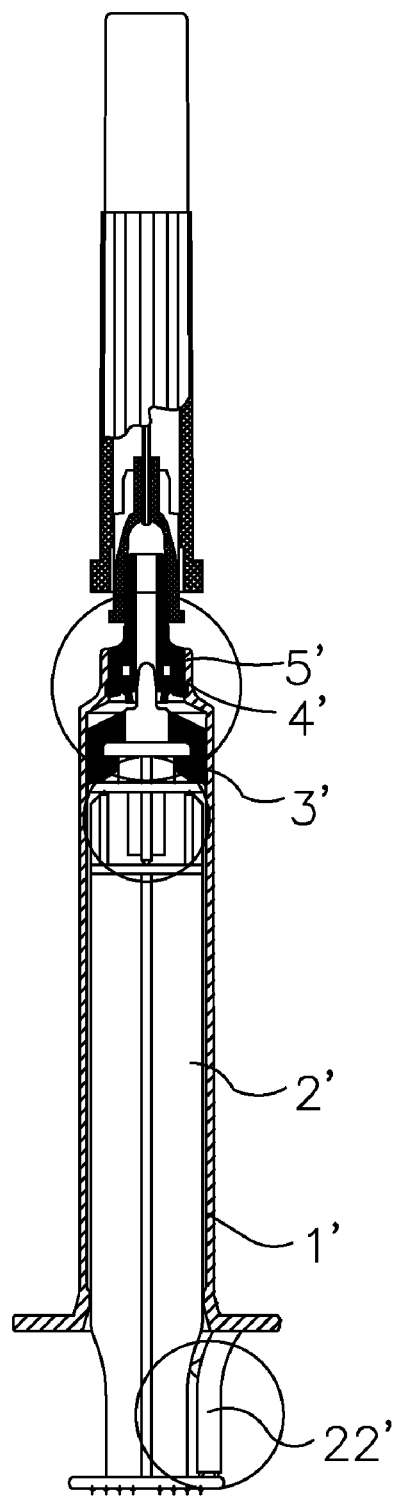
FIG. 12 is a sectional view showing the second embodiment of the present invention.
Figure 13:
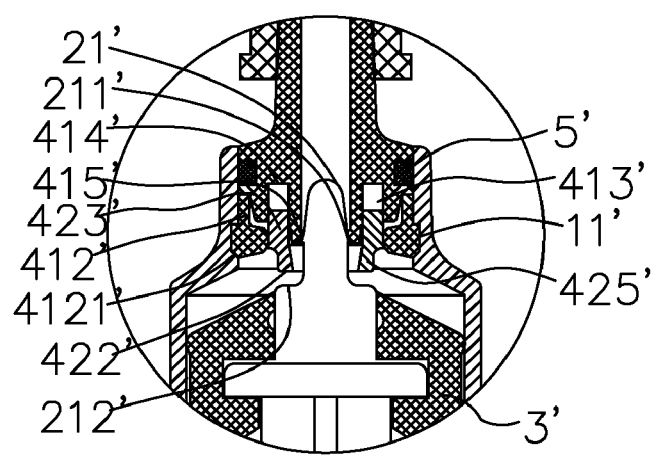
FIG. 13 is an enlarged sectional view of FIG. 12.
Figure 14:
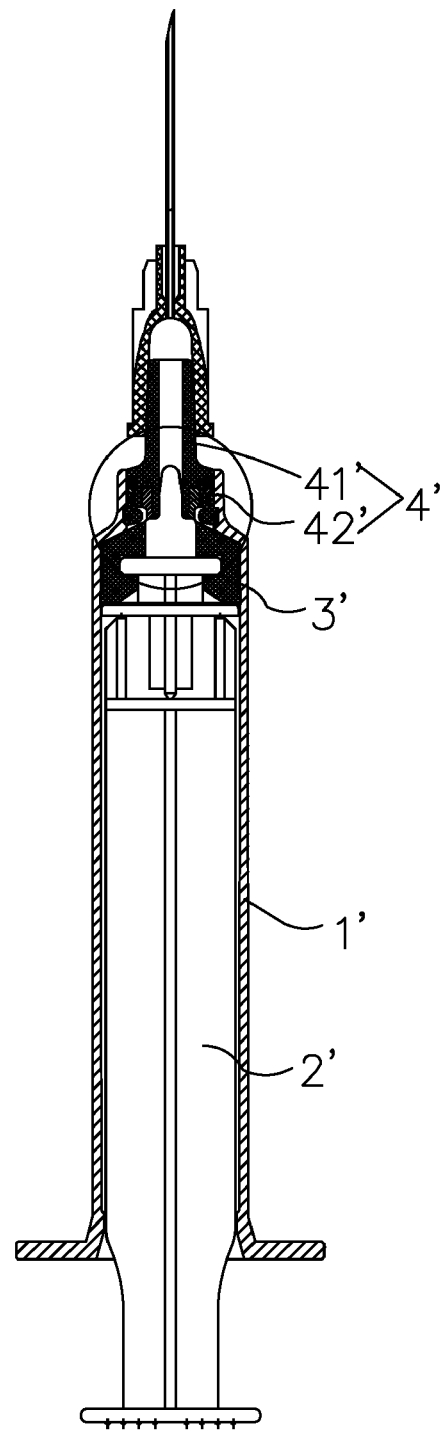
FIG. 14 is a sectional view showing the state of injecting operation of the present invention.
Figure 15:
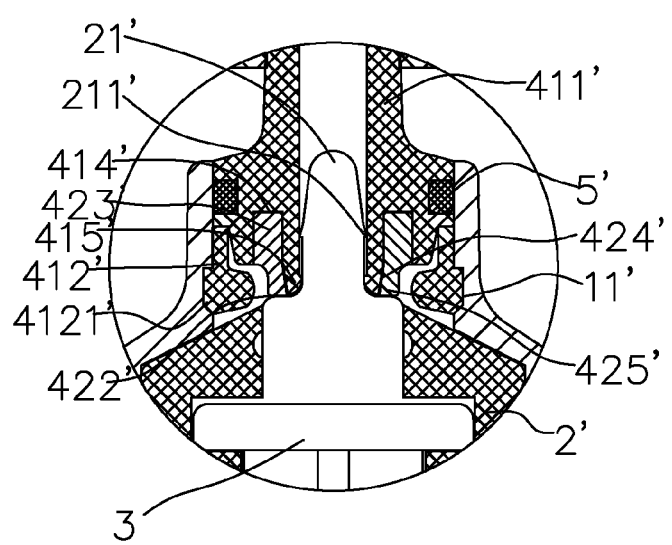
FIG. 15 is an enlarged sectional view showing of FIG. 14.

Referring to FIG. 12 to FIG. 15, the second embodiment of the present invention declares a safety syringe, which is typically consisted of a tube 1', a piston 3' fitting into the inside of the tube 1', a plunger 2' driving the piston 3' moving axially, and a needle holder 4'.

Said needle holder 4' is typically comprised of a cone base 41' and a seat 42'. Wherein, said cone base 41' has a Roll cone head with 6:100 taper for matching to diversity of standard needles. Said cone base 41' also has two elastic catching lugs 412' built on the external bottom side, coordinating to said elastic catching lugs 412', said tube 1' has a ring-groove 11' built on the corresponding position; said elastic catching lug 412' engaging into the inside of the ring-groove 11' of the hollow tube 1' can be in rectangle, ladder, circle, ellipse or polygon in sectional view, in this embodiment, said elastic catching lug 412' has a right upper-edge engaging portion 4121' and a low beveled surface for matching to the ring-groove 11' of the tube 1'. Said cone base 41' also has an elastic clamper 415' built on the internal low side wall, and an internal ring-groove 413' built on along the inside bottom rim; there is an O-ring 5 attached on the contacting surface between said cone base 41 and the tube 1.

Said seat 42' located at hollow cavity of the ring-groove 413' of said cone base 41' by the socket-joint stretches into the inside of the ring-groove 413' with the upper portion as assembling. Said seat 42' also has a column head 423' built on the external wall of the top end for matching with the elastic catching lugs 412' of the cone base 42', and a circumferential notch 425' built on the bottom, within the size of the circumferential notch 425' is in excess of the returning course of the elastic catching lugs 412' of the cone base 41'. In combination, said seat 42' is pushed upward axially from the bottom of said cone base 41' to extrude the elastic catching lugs 412' of the cone base 41' outward with the column head 423' to support the elastic catching lugs 412' engaging into the inside of the ring-groove 11' of the tube 1' so that the seat 41' is located on the inside of the tube 1' tightly without any possible to move and turn in any direction.

Said plunger 2' has a conical head 21' built on the front end, and said conical head 21' has a circular barb 211' built on the middle portion, as finishing the injection operation, said circular barb 211' exactly gets the topside of the elastic clamper 421' of said seat 42' so that they are interlocked together. Said plunger 2' has three knock-off notches A B C built on different surfaces at the front portion for keeping the trunk rigidity and facilitating to molding and breaking up as drawing with a bit force. Said plunger 2' also has a safety baffle 22' built on the rear end for preventing the syringe from self-destroying unexpectedly before use in a mistake operation in the packing or transportation; it works as a protection device. On the other hand, said safety baffle 22' has three knock-off points E F G for facilitating to breaking off after use.

As finishing sucking operation, break off the safety baffle 22'. But in injection operation, after the plunger 2' pushed moves a certain distance, the crowned conical head 21' crowds out said elastic clamper 415' of the cone base 41', and stretches into the hollow inner cavity of the cone base 41' until the injection operation is finished, in this time, the circular barb 211' exactly gets the inside of the elastic clamper 415' of said cone base 41', at this time, the beveled surface 423' at the inner bottom edge of the seat 42' just backs up the back of the elastic clamper 415' tightly so that they are interlocked together. meanwhile the front shoulder 212' of the plunger 2' runs into the lowest end 422' of the seat 42' to push the seat 41' continuously to get the top stopping point 414' of the ring-groove 413' of the cone base 41' (until the injection operation is finished), at that time, the column head 423' has departed from contacting with the elastic catching lugs 412', the elastic catching lugs 412' are withdrew back to the circumferential notch 425' of the seat 42' so as to disengage with the ring-groove 11' of the tube 1', at this time, just need to overcome the friction of the O-ring 5' and the inside wall of the tube 1', the seat 42' can be continued to move down until the whole needle is drew into the inside of the tube 1' by pulling down the plunger 2' to carry out self-destroying function.

Figure 16:
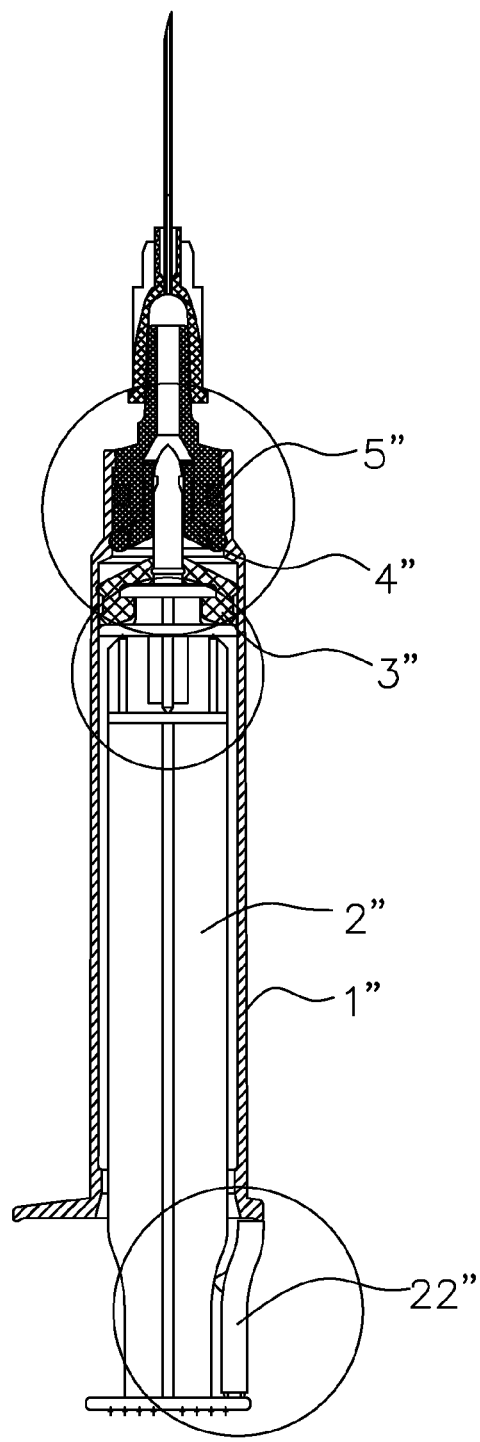
FIG. 16 is a sectional view showing the third embodiment of the present invention.
Figure 17:
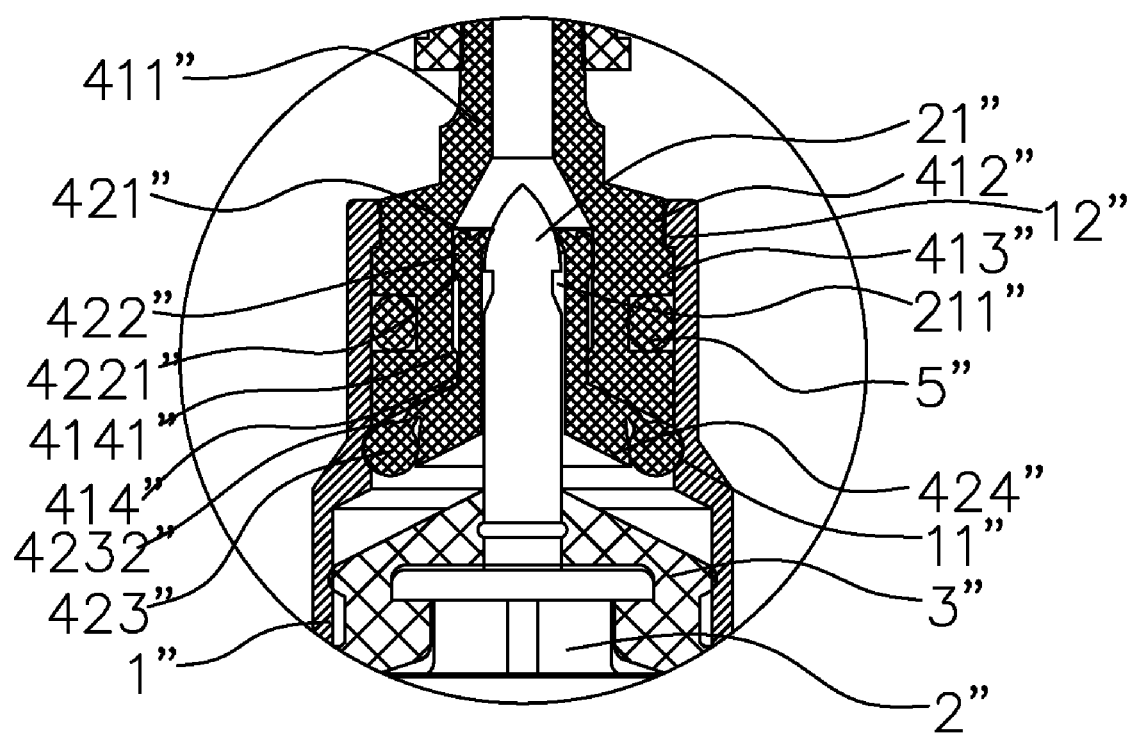
FIG. 17 is an enlarged sectional view of FIG. 16.
Figure 18:
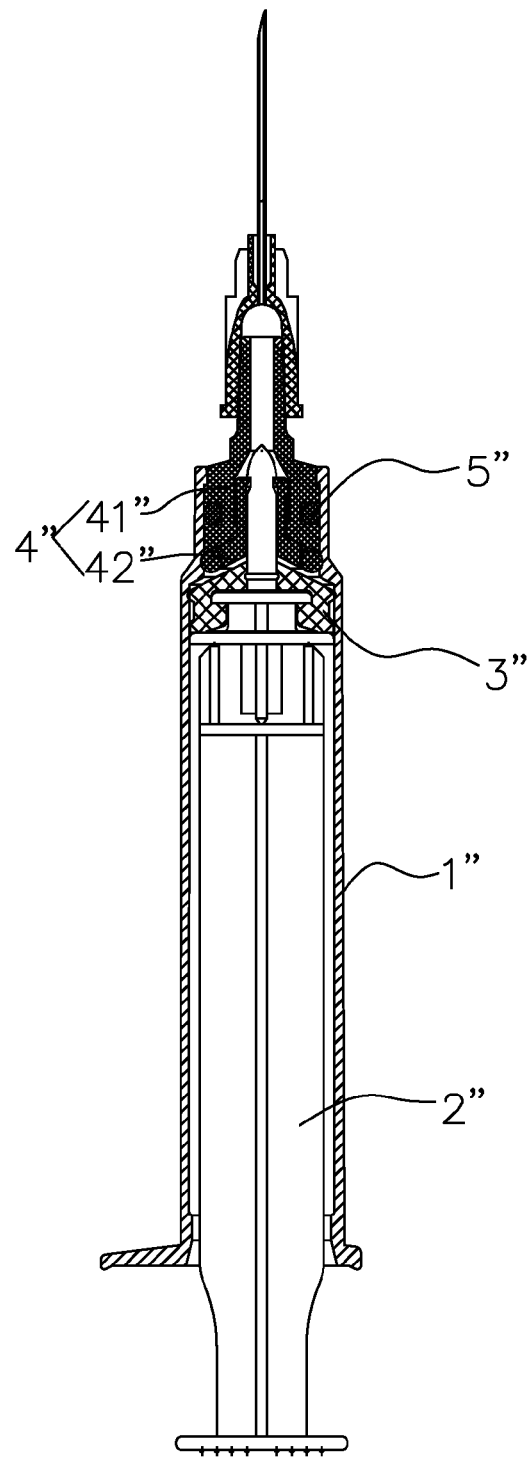
FIG. 18 is a sectional view showing the state of injection operation of the third embodiment of the present invention.
Figure 19:
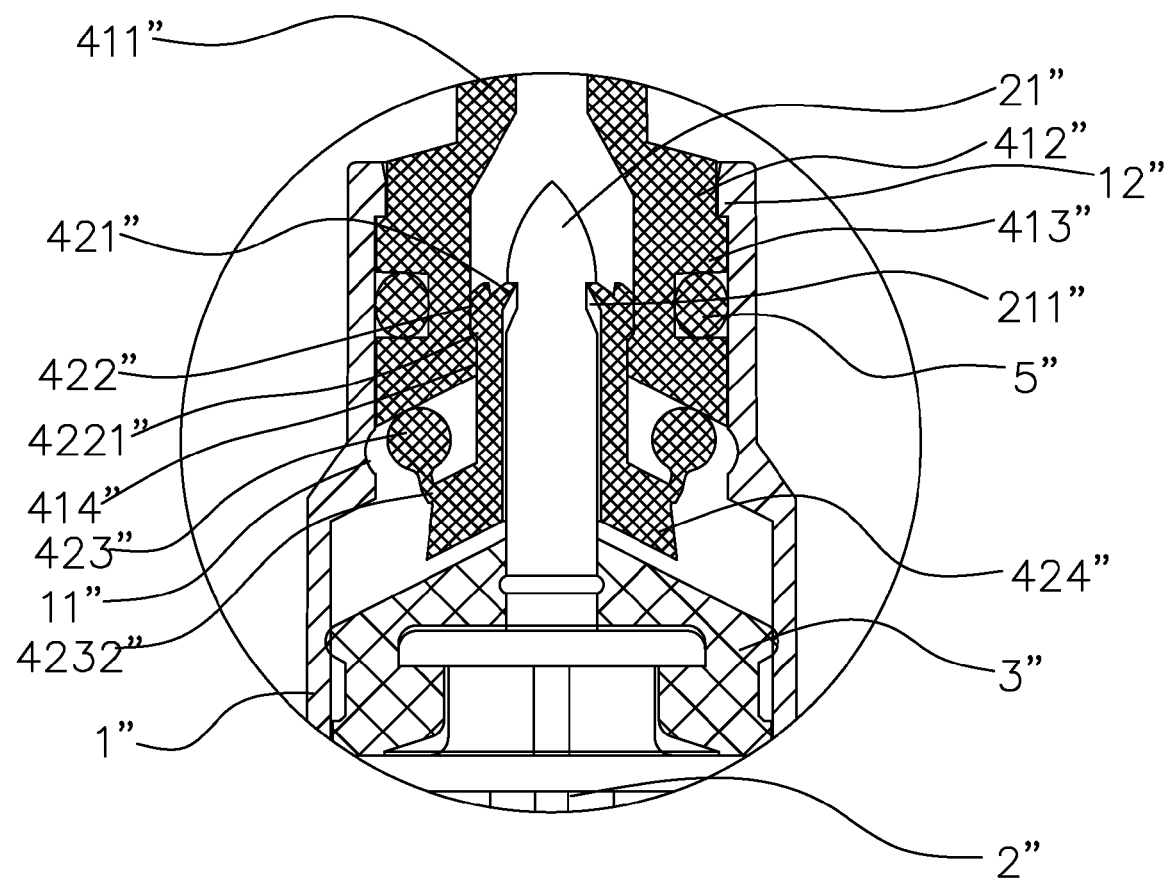
FIG. 19 is an enlarged sectional view of FIG. 18.

Referring to FIG. 16 to FIG. 19, the third embodiment of the present invention provides a safety syringe, which is typically consisted of a tube 1", a piston 3" fitting into the inside of the tube 1", a plunger 2" driving the piston 3" moving axially, and a needle holder 4".

Said needle holder 4" is typically comprised of a cone base 41" and a seat 42". Wherein, said cone base 41" has a Roll cone head with 6:100 taper for matching to diversity of standard needles. Said cone base 41" also has a polygon flange 412" built on the external upper edge for engaging with a flange 12" built on the inner top edge of said tube 1"; the engaging portion of said polygon flange 412" can be in rectangle, ladder, circle, ellipse or polygon in sectional view, in this embodiment, said polygon flange 412" is in cube shape for preventing the needle from rotating on the cone base 41"; said cone base 41" is located on the inside of the top end of the tube 1" with the external polygon flange 412", there is a shoulder 4121" formed between the two flanges 412" 413" of the cone base 41" for locating on the inside of the flange 12" of the tube 1" to prevent the cone base 41" from pushing out from the front end of the tube 1" as injecting. Said cone base 41" also has an internal convex edge 414" built on the internal low side wall, and an internal ring-groove 413" built on along the inside bottom rim; there is an O-ring 5" attached on the contacting surface between said cone base 41" and the tube 1".

Said seat 42" located at hollow cavity of said cone base 41" is made of elastic material, in which an elastic clamper 421" is built on the internal front edge, and a front flange 422" is built on the external front edge outward for fitting into the internal hole of said cone base 41", within the diameter of said front flange 422" is bigger than the inner diameter of the internal convex edge 414" of said cone base 41". Said seat 42" has two elastic catching lugs 423" built on the external bottom portion symmetrically, coordinating to the elastic catching lugs 423", the tube 1" has a ring-groove 11" built upon for engaging together; the engaging portion of said elastic catching lug 423" and the ring-groove 11" of the tube 1" can be in rectangle, ladder, circle, ellipse or polygon in sectional view, in this embodiment, said elastic catching lug 423" is in circle in the sectional view facilitating to mate together tightly. The elastic catching lugs 423" can be spread out or withdrew back to the center; as spreading our, they engage with the ring-groove 11" of said tube 1" to locate said cone base 41" on the tube 1" tightly; but as drawing back, they can disengage with the ring-groove 11" of said tube 1" to release the cone base 41" from the tube 1". In combination, said seat 42" is pushed upward axially from the bottom of said cone base 41 to extrude the front flange 422" under an extra force coming from the internal convex edge 414" of said cone base 41" to distort until the whole front flange 422" passes through the internal convex edge 414" to restore the original state. Meanwhile in the term of pushing up the seat 42", the low flange 424" pushes the self-substantial elastic catching lugs 423" built on the external side outward, and supports the elastic catching lugs 423" engaging into the inside of the ring-groove 11" of the tube 1" so that the seat 41" is located on the intermediate place between the tube 1" and the seat 42" tightly without any possible to move and turn in any direction.

Said plunger 2" has a conical head 21" built on the front end, and said conical head 21" has a circular barb 211" built on the middle portion, as finishing the injection operation, said circular barb 211" exactly gets the topside of the elastic clamper 421" of said seat 42" so that they are interlocked together. Said plunger 2" has three knock-off notches A B C built on different surfaces alternatively at the front portion for keeping the trunk rigidity and facilitating to molding and breaking up as drawing with a bit force. Said plunger 2" also has a safety baffle 22" built on the rear end for preventing the syringe from self-destroying unexpectedly before use in a mistake operation in the packing or transportation; it works as a protection device. On the other hand, said safety baffle 22" has three knock-off points E F G for facilitating to breaking off after use.

As finishing sucking operation, break off the safety baffle 22". But in injection operation, after the plunger 2" pushed moves a certain distance, the crowned conical head 21" crowds out said elastic clamper 421" of the seat 42", and stretches into the hollow inner cavity of the seat 42" until the injection operation is finished, in this time, the circular barb 211" exactly gets the inside of the elastic clamper 421" of said seat 42" so that they are interlocked together. Next, pull backward the plunger 2", by means of the interlocking of the circular barb 211" and the elastic clamper 421", the seat 42" is drew to move downward, when the upper stopping point 4221" of the front flange 422" of the seat 42" is drew to touch with the low stopping point 4141" of the internal convex edge 414" of the cone base 41", the low flange 424" is departed from the elastic catching lugs 423" so that the elastic catching lugs 423" are withdrew back inward to slide out from the ring-groove 11" of the tube 1", at this time, just need to overcome the friction of the O-ring 5" and the inside wall of the tube 1", the seat 42" can be continued to move down until the whole needle is drew into the inside of the tube 1" to carry out self-destroying function.

In one word, the safety syringe provided by the present invention can be withdrew into the inside of the tube, and also suit to match to diversity of standard needles for replacing, it also has simple structure, easy manufacturing and convenient use with high safeness features.

I claim:

1. A safety syringe comprising
   a hollow tube with a front end, an inside, and an inside wall,
   a plunger, with a tip end adapted to fit into said inside of said hollow tube,
   a rubber piston attached on said tip end of said plunger,
   a needle holder attached to said front end of said hollow tube,
   a locating ring-groove formed on said inside wall near said front end of said hollow tube for catching said needle holder, and
   one or more O-ring attached between said needle holder and said inside of said hollow tube; wherein
   said plunger comprises a conical head on the front end thereof, which is formed with a barb in the middle portion of said conical head,
   said needle holder further comprises
      a cone base, with a hollow inside, an inner wall and an outside bottom wall, further comprising
         a Roll cone for fitting into a needle, and
      a seat, with an internal front end and an outside front end, adapted to fit into said hollow inside of said cone base, wherein
   said cone base further comprises
      a circular base for fitting into said inside of said hollow tube,
      an internal convex edge formed on said inner wall of said cone base, and
      several elastic catching lugs formed on said outside bottom wall of said cone base, adapted to engage with said locating ring-groove of said hollow tube, and
   said seat further comprises
      an elastic clamper formed on said internal front end of said seat,
      a front flange formed on said outside front end of said seat and adapted to get over said internal convex edge of said cone base during assembly and to engage with said internal convex edge after assembly, and
      a middle flange formed on the middle portion of said seat for supporting outwards said elastic catching lugs of said cone base.

2. A safety syringe as claimed in claim 1, wherein said elastic catching lugs either spread outs or withdraw in; when spreading out, said elastic catching lugs engage to the inside of said ring-groove of said hollow tube to secure said cone base onto said hollow tube; when withdrawing in, said elastic catching lugs slide out from said ring-groove of said hollow tube to release said cone base from said hollow tube.

3. A safety syringe as claimed in claim 1, wherein the engaging portions of said elastic catching lug and said ring-groove of said hollow tube is in the shape of a rectangle, a ladder, a circle, an ellipse or a polygon in a sectional view.

4. A safety syringe as claimed in claim 1, wherein said plunger comprises knock-off notches located on the surfaces at the middle portion thereof.

5. A safety syringe as claimed in claim 1, wherein said internal convex edge disposed on the inside wall of said cone base is matched between said front and middle flanges of said seat and freely moves in there, and also mates with said front flange of said seat.

6. A safety syringe comprising
   a hollow tube with a front end, an inside, and an inside wall,
   a plunger, with a tip end, adapted to fit into said inside of said hollow tube, comprising a conical head on said front end of said plunger, which is formed with a barb on the middle portion of said conical head,
   a rubber piston attached on said tip end of said plunger,
   a needle holder, attached on said front end of said hollow tube,
   a locating ring-groove, and
   one or more O-ring; wherein
   said one or more O-ring is attached between said needle holder and said inside of said hollow tube;
   said hollow tube is formed on said inside wall thereof near said front end thereof
   with said locating ring-groove for catching said needle holder;
   said needle holder comprises
      a cone base with a hollow inside, an inside bottom wall, an outside bottom wall and a top portion, and
      a seat, with a bottom, adapted to fit into said hollow inside of said cone base,
   wherein
   said cone base further comprises
      a Roll cone for fitting into a needle,
      a circular base for fitting into said inside of said hollow tube, one or more clamper formed on said inside bottom wall of said cone base, several elastic catching lugs formed on said outside bottom wall of said cone base, adapted to engage with said locating ring-groove of said hollow tube, and a ring-groove formed in said inside of said cone base for receiving said seat with the depth thereof longer than the sum of the fitting segment of the top portion of said seat and the distance of push-up; and said seat further comprises a column head with a top portion and a lower portion, and a circumferential notch formed on said bottom of said seat, wherein the size of said circumferential notch is in excess of the returning course of said elastic catching lugs of said cone base, and said column head is sized in such a way that, before an injection operation is finished, the top portion of said column head extends into said ring-groove of said cone base and the lower portion of said column head supports outwards said elastic catching lugs of said cone base, and when the injection operation is finished, said column head extends into said ring-groove of said cone base to the extent that said elastic catching lugs of said cone base faces said circumferential notch;

said plunger further comprises a front shoulder designed to push said seat into said ring-groove of said cone base when the injection operation is finished.

7. A safety syringe as claimed in claim 6, wherein said elastic catching lugs either spreads out or withdraw in; when spreading out, said elastic catching lugs engage to the inside of said ring-groove of said hollow tube to secure said cone base to said hollow tube; when withdrawing in, said elastic catching lugs slide out from said ring-groove of said hollow tube to release the cone base from said hollow tube.

8. A safety syringe as claimed in claim 6, wherein the engaging portions of said elastic catching lug and said ring-groove of said hollow tube is in the shape of a rectangle, a ladder, a circle, an ellipse or a polygon in a sectional view.

9. A safety syringe as claimed in claim 6, wherein said seat fitting into the inside of said cone base moves in the gap between said elastic catching lugs and the ring-groove, as getting to lowest point, the inside beveled surface of the bottom end of the seat exactly backs up the back of the elastic clamper of said cone base up tightly.

10. A safety syringe comprising a hollow tube with a front end, an inside and a front internal flange, a plunger, with a tip end, adapted to fit into said inside of the hollow tube, a rubber piston attached on said tip end of the plunger, a needle holder attached to said front end of said hollow tube, a locating ring-groove, and one or more O-ring; wherein said one or more O-ring is attached between said needle holder and said inside of said hollow tube;

said hollow tube comprises said locating ring-groove formed on said inside wall near said front end of said hollow tube for catching said needle holder and a front internal flange;

said plunger comprises a conical head on the front end thereof, and said conical head is formed with a barb on the middle portion thereof;

said needle holder comprises a cone base, comprising a Roll cone for fitting into a needle, a circular base for fitting into said inside of said hollow tube, an upper flange formed on the outside wall of said cone base for matching to said front internal flange of said hollow tube, a middle flange matins to the hollow cavity of said hollow tube, so between said upper and middle flanges a flat mesa is formed, and an internal convex edge formed on the bottom portion of the inside wall of said cone base, and a seat, with an internal front end and an outside front end, adapted to fit into said hollow inside of said cone base, comprising an elastic clamper formed on the internal front end of said seat, a front flange formed on said outside front end of said seat and adapted to get over said internal convex edge of said cone base during assembly and to engage with said internal convex edge after assembly, and several elastic catching lugs formed on the outside bottom wall of said seat and adapted to engage with said locating ring-groove of said hollow tube.

11. A safety syringe as claimed in claim 10, wherein said elastic catching lugs either spread out or withdraw in; when spreading out, said elastic catching lugs engage to the inside of said ring-groove of said hollow tube to secure said cone base to said hollow tube; when withdrawing in, said elastic catching lugs slide out from said ring-groove of said hollow tube to release said cone base from said hollow tube.

12. A safety syringe as claimed in claim 10, wherein the engaging portions of said elastic catching lug and said ring-groove of said hollow tube is in the shape of a rectangle, a ladder, a circle, an ellipse or a polygon in a sectional view.

13. A safety syringe as claimed in claim 10, wherein said internal convex edge disposed on the inside wall of said cone base is matched between said front and middle flanges of said seat and freely moves in there, and also mates with said front flange of said seat.

14. A safety syringe as claimed in claim 10, wherein the flange of said hollow needle is a right step engaging on the front flange of said cone base to overlap the middle flange, wherein the shape of the engaging portion in sectional view is in the shape of a rectangle, a ladder, a circle, an ellipse or a polygon.

* * * * *